United States Patent [19]

Effland et al.

[11] Patent Number: 5,260,319
[45] Date of Patent: Nov. 9, 1993

[54] THIENOBENZOXEPINS AND NAPHTHOTHIOPHENES

[75] Inventors: Richard C. Effland, Bridgewater; David G. Wettlaufer, Phillipsburg, both of N.J.

[73] Assignee: Hoechst-Roussel Pharmaceuticals Incorporated, Somerville, N.J.

[21] Appl. No.: 35,095

[22] Filed: Mar. 19, 1993

Related U.S. Application Data

[62] Division of Ser. No. 648,496, Jan. 30, 1991, Pat. No. 5,227,388, which is a division of Ser. No. 457,132, Dec. 26, 1989, Pat. No. 5,006,536.

[51] Int. Cl.$^5$ .................. A61K 31/445; C07D 409/06
[52] U.S. Cl. .................... 514/326; 514/422; 546/213; 548/527
[58] Field of Search ................. 546/213; 548/527; 514/326, 422

[56] References Cited

U.S. PATENT DOCUMENTS

| | | | |
|---|---|---|---|
| 4,025,640 | 5/1977 | Fadden | 546/90 |
| 4,128,641 | 12/1978 | Itil | 546/353 |
| 4,282,365 | 8/1981 | Rokach | 548/252 |
| 4,294,828 | 10/1981 | Thominet | 546/269 |
| 4,312,868 | 1/1982 | McCall | 546/199 |
| 4,595,689 | 6/1986 | Boris | 546/269 |
| 5,010,087 | 4/1991 | Oshima et al. | 514/427 |

FOREIGN PATENT DOCUMENTS

| | | |
|---|---|---|
| 0074304 | 3/1983 | European Pat. Off. . |
| 0119541 | 9/1984 | European Pat. Off. . |
| 1371443 | 7/1964 | France . |

OTHER PUBLICATIONS

J. T. Strupczewski, et al., Journal of Medicinal Chemistry, 28, 761 (1985) published in the U.S. and entitled "Synthesis and Neuroleptic Activity of 3-(1-Substituted-4-piperidinyl)-1,2-benzisoxazoles".

"Medicinal Chemistry", A. Burger, Edition, Interscience Publishers, Inc., New York, N.Y., 1960, pp. 75 and 81 of Chapter 8, entitled Isosterism and Bio-isosterism.

K. Thomae, Chemical Abstracts, 64, 19575 (1966) published in the U.S. and entitled "5,6-Dihydromorphanthridines".

C. W. Thornber, "Isosterism and Molecular Modification in Drug Design", Chemical Society Reviews, 8,563 to 565 (1979), published in the United Kingdom.

Primary Examiner—C. Warren Ivy
Assistant Examiner—Celia Chang
Attorney, Agent, or Firm—Raymond R. Wittekind

[57] ABSTRACT

Novel thienobenzoxepins and naphthothiophenes, intermediates and processes for the preparation thereof, and methods of alleviating pain utilizing compounds or compositions thereof are disclosed.

7 Claims, No Drawings

THIENOBENZOXEPINS AND NAPHTHOTHIOPHENES

This is a division of application Ser. No. 07/648,496 filed Jan. 30, 1991 now U.S. Pat. No. 5,227,388 which is a division of application Ser. No. 07/457,132 filed Dec. 26, 1989, now U.S. Pat. No. 5,006,536.

The present invention relates to thienobenzoxepins. More particularly, the present invention relates to thieno[3,2-c][1]benzoxepins of formula 1

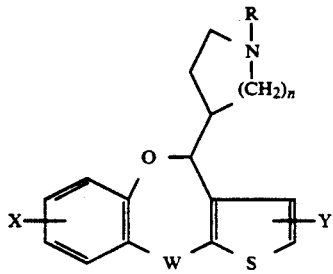

wherein R is loweralkyl or arylloweralkyl; X and Y are independently hydrogen, loweralkyl, halogen, loweralkoxy, or trifluoromethyl; W is $CH_2$, CHOH, or C=O; and n is 1 or 2; an optical isomer or pharmaceutically acceptable salt thereof, which are useful for alleviating pain, alone or in combination with adjuvants.

The present invention also relates to naphthothiophenes. More particularly, the present invention also relates to naphtho[2,3-b]thiophenes of formula 2

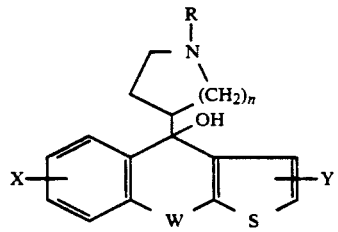

wherein R is loweralkyl or arylloweralkyl, X and Y are independently hydrogen, loweralkyl, halogen, loweralkoxy, or trifluoromethyl; W is $CH_2$, CHOH, or C=O, and n is 1 or 2; an optical isomer or pharmaceutically acceptable salt thereof.

Subgeneric to the thieno[3,2-c][1]benzoxepins and naphtho[2,3-b]thiophenes of the present invention are compounds of formulas 1 and 2 wherein W is C=O and n is 2.

Also included in the present invention are 4-piperidinyl- or 3-pyrrolidinylthienylmethanols of formula 3.

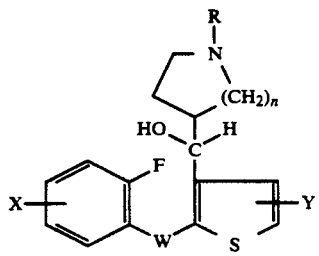

wherein R is loweralkyl arylloweralkyl; X and Y are independently hydrogen, loweralkyl, halogen, loweralkoxy, or trifluoromethyl; W is $CH_2$, CHOH, or C=O; and n is 1 or 2; an optical isomer or pharmaceutically acceptable addition salt thereof; which are useful for alleviating pain, alone or in combination with adjuvants, and as intermediates for the synthesis of the present thieno[3,2-c][1]benzoxepins and naphtho[2,3-b]thiophenes.

Subgeneric to the thienylmethanols of the present invention are compounds of formula 3 wherein n is 2.

As used throughout the specification and appended claims, the term "alkyl" refers to a straight or branched chain hydrocarbon radical containing no unsaturation and having 1 to 8 carbon atoms such as methyl, ethyl, 1-propyl, 2-propyl, 1-butyl, 1-pentyl, 2-pentyl, 3-hexyl, 4-heptyl, 2-octyl, and the like; the term "aryl" refers to a phenyl group or a phenyl group substituted by one or more alkyl, halogen, alkoxy or trifluoromethyl groups; the term "alkanol" refers to a compound formed by a combination of an alkyl group and a hydroxy radical. Examples of alkanols are methanol, ethanol, 1- and 2-propanol, 1,2-dimethylethanol, hexanol, octanol, and the like. The term "alkoxide" refers to an anion formed by removal of a proton from the hydroxyl moiety of an alkanol. Examples of alkoxides are methoxide, ethoxide, 1-propoxide, 2-propoxide, 1-butoxide, 1,1-dimethylethoxide (tertiary-butoxide), 1-pentoxide, 2-pentoxide, 3-hexoxide, 4-heptoxide, 2-octoxide, and the like; The term "alkoxy" refers to a monovalent substituent which consists of an alkyl group linked through an ether oxygen and having its free valence bond from the ether oxygen. Examples of alkoxy groups are methoxy, ethoxy, 1-propoxy, 2-propoxy, 1-butoxy, 1-pentoxy, 2-pentoxy, 3-hexoxy, 4-heptoxy, 2-octoxy, and the like; the term "halogen" refers to a member of the family consisting of fluorine, chlorine, bromine and iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diasteromeric salts of those instant compounds characterized by the presence of a basic amino group and an optically active acid, or by the synthesis from optically active precursors.

The present invention comprehends all optical isomers and racemic forms thereof and all geometric isomers of the compounds disclosed and claimed herein. The formulas of the compounds shown herein are intended to encompass all possible geometric and optical isomers of the compounds so depicted.

The novel thienobenzoxepins and naphthothiophenes of the present invention are prepared by the process illustrated in Reaction Scheme A.

To gain entry into the thieno[3,2-c][1]benzoxepin system, i.e., to prepare oxepins of formula 1, a thiophene carboxaldehyde of formula 4 is condensed with a Grignard reagent of formula 5

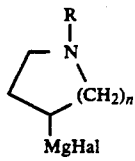

wherein R and n are as hereinbeforedescribed and Hal is bromo or chloro, prepared by the procedures described of J. T. Strupczewski, et al., *Journal of Medicinal Chemistry*, 28, 761(1985), to provide a carbinol 3 which is cyclized to oxepin 1. The condensation is conducted in an ethereal solvent such as, for example, diethyl ether, 1,2-dimethoxyethane, 2-methoxyethyl ether, dioxane, or tetrahydrofuran. Tetrahydrofuran is preferred. The condensation temperature is not critical; it is desirable, however, to perform the reaction at a temperature within the range of about −100° to about 50°0 C., a temperature within the range of about −78° to 25° C. being preferred.

The cyclization accomplished by treating a carbinol 3 with an alkali metal alkoxide in an ethereal solvent. Among alkali metal alkoxides there may be mentioned sodium, potassium, or lithium methoxides, ethoxides, 1- and 2-propoxides, 1,1-dimethylethoxides, and the like. Among ethereal solvents there may be mentioned 1,2-dimethoxyethane, 2-methoxyethyl ether, dioxane, tetrahydrofuran, and the like. Potassium 1,1-dimethylethoxide, i.e., potassium tertiary-butoxide, and tetrahydrofuran are the preferred alkali metal oxide and ethereal solvent respectively.

The cyclization proceeds readily at a temperature within the range of about −100° to about 25° C. to afford oxepin 1. The preferred cyclization temperature is about −78° to 0° C.

To elaborate a naphtho[2,3-b]thiophene 2, a carbinol 3 is cyclized by means of an alkali metal alkoxide (e.g., sodium, potassium, or lithium methoxides, ethoxides, 1- and 2-propoxides, 1,1-dimethylethoxides, and the like) in a dipolar aprotic solvent such as, for example, dimethylacetamide, dimethylformamide, hexamethylphosphoramide, dimethylsulfoxide, and the like or an ethereal solvent such as 1,2-dimethoxyethane, 2-methoxyethyl ether, dioxane, tetrahydrofuran and the like, at a temperature from about −25° to 25° C. Potassium 1,1-dimethylethoxide, i.e., potassium tertiary-butoxide, in dimethylformamide at a temperature of about 0° C. is the preferred reaction condition.

The precursors of the thieno[3,2-c][1]benzoxepins 1 and naphtho[2,3-b]thiophenes 2, i.e., the thiophene carboxaldehyde 4 and thiophene methanol 3 of the present invention, are prepared by procedures conventional in the art as illustrated in Reaction Schemes B and C. For example, condensation of thiophene carboxaldehyde dimethyl acetal wherein Y is hydrogen as the 2-lithio derivative with 2-fluorobenzoyl chloride 6 wherein X is hydrogen provides the ketoacetal 8 wherein X and Y are hydrogen which is converted by means of hydrogen chloride in ethanol to ketoaldehyde 9 wherein X and Y are hydrogen. Deketonization of the hydrazone of 8, prepared utilizing hydrazine hydrate, with potassium hydroxide in 2-hydroxyethanol affords acetal 10 wherein X and Y are hydrogen which is hydrolyzed by sulfuric acid to aldehyde 4 wherein X and Y are hydrogen. See Reaction Scheme B.

Similarly, condensation of 2-fluorobenzaldehyde 11 wherein X is hydrogen with the 2-lithio derivation of 3-thiophene carboxaldehyde dimethylacetal 7 wherein Y is hydrogen gives hydroxyacetal 12 wherein X and Y are hydrogen which is hydrolyzed by sulfuric acid to hydroxyaldehyde 13 and is converted by ethyl vinyl ether to methoxyethoxyaldehyde 14 wherein X and Y are hydrogen. Condensation of aldehyde 14 with Grignard reagent 5 provides methanol 15 which is hydrolyzed by hydrochloric acid to dimethanol 16.

REACTION SCHEME A

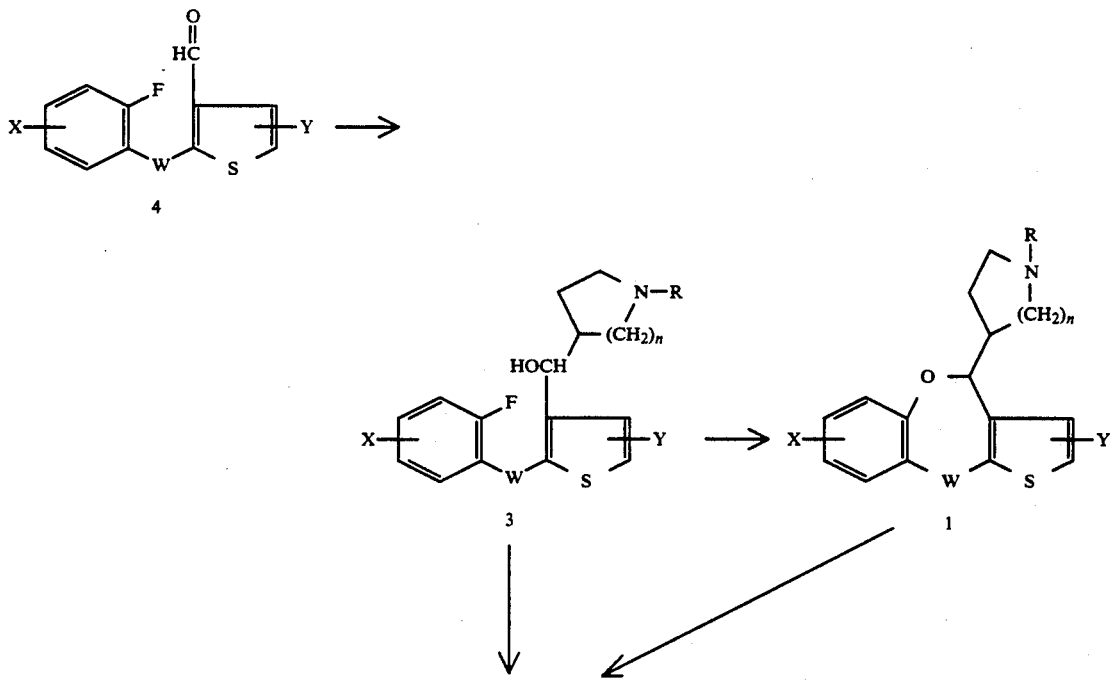

-continued
REACTION SCHEME A
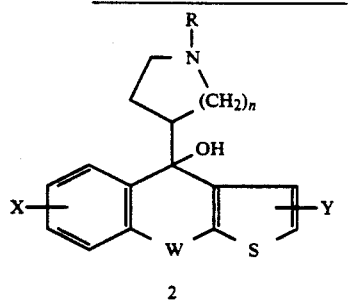
wherein R, W, X, Y and n are as hereinbeforedescribed
REACTION SCHEME B
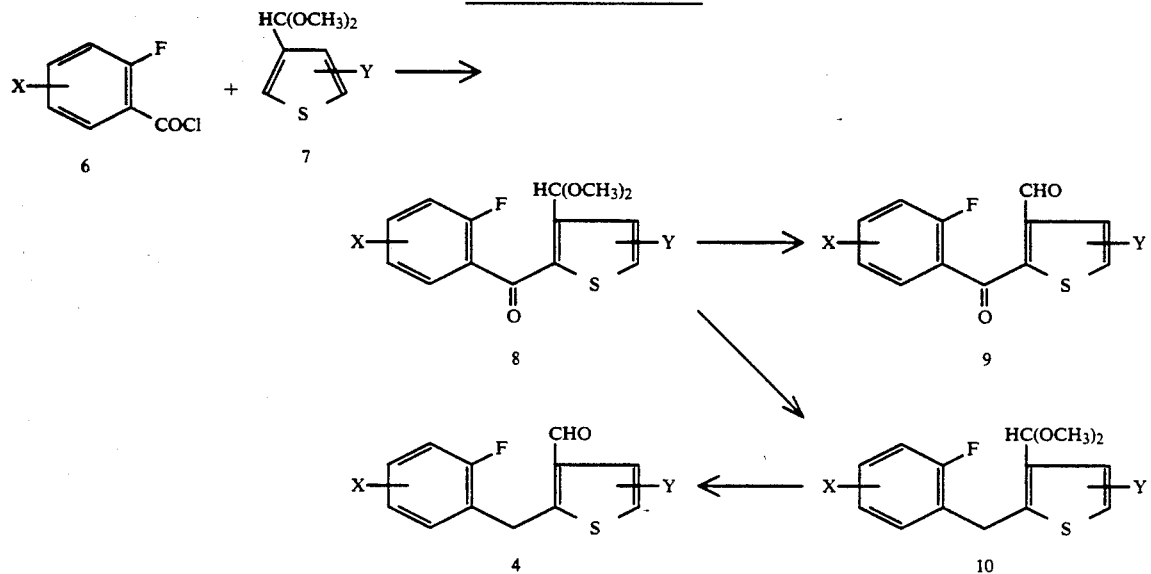
wherein X and Y are as hereinbeforedescribed
REACTION SCHEME C
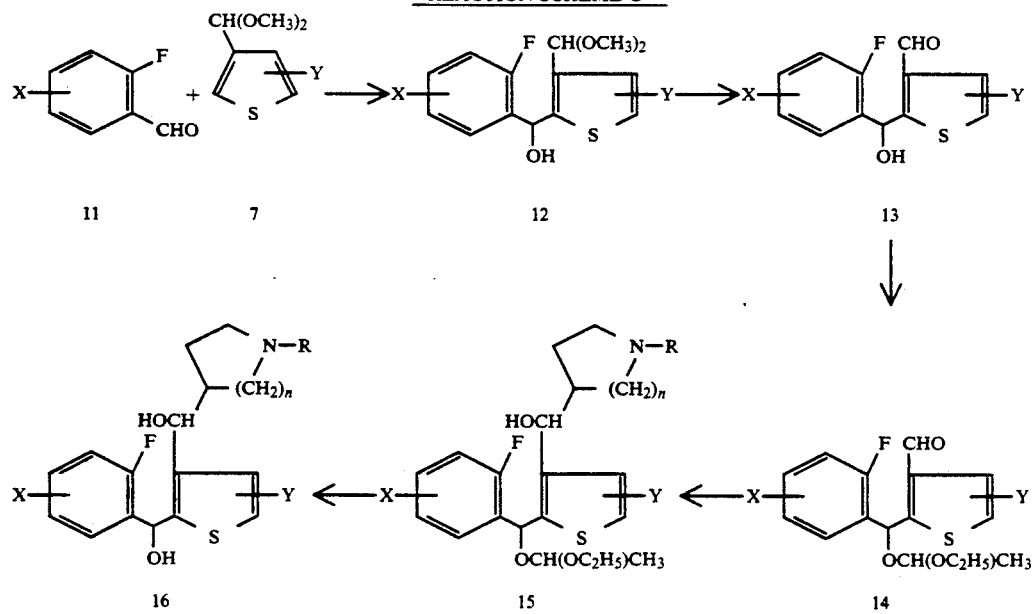

-continued
REACTION SCHEME C wherein R, X, Y, and n are as hereinbeforedescribed The thienobenzoxepins, naphthothiophenes, and thienylmethanols of the present invention are useful as analgetics due to their ability to alleviate pain in mammals. The analgetic utility is demonstrated in the phenyl-p-quinone writhing assay in mice, a standard assay for analgetic activity [*Proc. Soc. Exptl. Biol. Med.*, 95, 729 (1957)]. Thus, for instance, at a subcutaneous dose of 20 mg/kg the percent decrease in writhes in mice produced in this assay is as shown in the Table.

TABLE

| Compound | Dose (mg/kg) | Analgetic Activity Percent Decrease in Writhes |
| --- | --- | --- |
| (2-fluorophenyl)[3-[(1-methyl-4-piperidinyl)hydroxymethyl]-2-thienyl]methanone | 20 | 35 |
| α-[2-[(2-fluorophenyl)methyl]-3-thienyl]-1-methyl-4-piperidine-methanol | 20 | 47 |
| 4-(1-methyl-4-piperidinyl thieno[3,2-c][1]benzoxepin-10(4H)-one fumarate | 20 | 29 |
| 7-fluoro-4-(1-methyl-4-piperidinyl)thienyo[3,2-c][1]benzoxepin-10(4H)-one sesquifumarate | 20 | 36 |
| 4-hydroxy-4-(1-methyl-4-piperidinyl)naphtho[2,3-b]thiophen-9(4H)-one hydrochloride | 20 | 33 |
| propoxyphene | 3.9 | 50 |

Compounds of the present invention include:
a. 7-ethyl-4-(1-methyl-4-piperidinyl)-thieno[3,2-c][1]benzoxepin-10(4H)-one;
b. 8-methyoxy-4-(1-methyl-4-piperidinyl)-thieno[3,2-c][1]benzoxepin-10(4H)-one;
c. 4-(1-methyl-4-piperidinyl)-9-trifluoromethyl-thieno[3,2-c][1]benzoxepin-10(4H)-one;
d. 4,10-dihydro-4-(1-methyl-4-piperidinyl)thieno[3,2-c][1]benzoxepine;
e. 4,10-dihydro-4-(1-methyl-4-piperidinyl)thieno[3,2-c][1]benzoxepin-10-ol;
f. 6-ethyl-4-hydroxy-4-(1-methyl-4-piperidinyl)-naphtho[2,3-b]thiophen-9(4H)-one;
g. 4-hydroxy-7-methoxy-4-(1-methyl-4-piperidinyl)-naphtho[2,3-b]thiophen-9(4H)-one;
h. 8-fluoro-4-hydroxy-4-(1-methyl-4-piperidinyl)-naphtho[2,3-b]thiophen-9(4H)-one;
i. 4-hydroxy-4-(1-methyl-4-piperidinyl)-5-trifluoromethylnaphtho[2,3-b]thiophen-9(4H)-one;
j. 4,9-dihydro-4-hydroxy-4-(1-methyl-4-piperidinyl)-naphtho-[2,3-b]thiophene;
k. 4,9-dihydro-4-hydroxy-4-(1-methyl-4-piperidinyl)-naphtho-[2,3-b]thiophen-9-ol;
l. 4-(1-methyl-3-pyrrolidinyl)thieno[3,2-c][1]benzoxepin-10(4H)-one;
m. 4-hydroxy-4-(1-methyl-3-pyrrolidinyl)naphtho-[2,3-b]thiophen-9(4H)-one;
n. 2-ethyl-4-(1-methyl-4-piperidinyl)-thieno[3,2-c][1]benzoxepin-10(4H)-one;
o. 2-fluoro-4-(1-methyl-4-piperidinyl)-thieno[3,2-c][1]benzoxepin-10(4H)-one;
p. 3-methoxy-4-(1-methyl-4-piperidinyl)-thieno[3,2-c][1]benzoxepin-10(4H)-one;
q. 4-(1-methyl-4-piperidinyl)-3-trifluoromethyl-thieno[3,2-c][1]benzoxepin-10(4H)-one;
r. 4-hydroxy-2-methyl-4-(1-methyl-4-piperidinyl)-naphtho[2,3-b]thiophen-9(4H)-one;
s. 3-fluoro-4-hydroxy-4-(1-methyl-4-piperidinyl)-naphtho[2,3-b]thiophen-9(4H)-one;
t. 4-hydroxy-3-methoxy-4-(1-methyl-4-piperidinyl)-napththo[2,3-b]thiophen-9(4H)-one;
u. 4-hydroxy-4-(1-methyl-4-piperidinyl)-5-trifluoromethylnaphtho-[2,3-b]thiophen-9(4H)-one;
v. (2-fluoro-3-methylphenyl)[3-[(1-methyl-4-piperidinyl)hydroxymethyl]-2-thienyl]methanone;
w. (2-fluoro-3-methylphenyl)[3-[(1-methyl-4-piperidinyl)hydroxymethyl]-2-thienyl]methanone;
x. (2,5-difluorophenyl)[3-[(1-methyl-4-piperidinyl)hydroxymethyl]-2-thienyl]methanone;
y. (2-fluoro-5-methoxyphenyl)[3-[(1-methyl-4-piperidinyl)hydroxymethyl]-2-thienyl]methanone;
z. (2-fluoro-4-methoxyphenyl)[3-[(1-methyl-4-piperidinyl)hydroxymethyl]-2-thienyl]methanone;
aa. (2-fluoro-6-trifluoromethylphenyl)[3-[(1-methyl-4-piperidinyl)hydroxymethyl-2-thienyl]methanone;
bb. (2-fluorophenyl-4-trifluoromethyl)[3-[(1-methyl-4-piperidinyl)hydroxymethyl]-2-thienyl]methanone; and
cc. (2-fluorophenyl)[3-[(1-methyl-3-pyrroldinyl)hydroxymethyl]-2-thienyl]methanone.

Analgesia production is achieved when the present thienobenzoxepins, naphthothiophenes, and thienylmethanols are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Effective amounts of the compounds of the invention may be administered to a subject by any one of various methods, for example, orally as in capsules or tablets, parenterally in the form of sterile solutions or suspensions, and in some cases intravenously in the form of sterile solutions. The thienobenzoxepins, naphthothiophenes, and thienylmethanols of the present invention, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, and the like, and salts of tribasic carboxylic acids such as, for example, carboxysuccinic acid, citric acid and the like.

Effective quantities of the compounds of the invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatine; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the active compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following Examples are for illustrative purposes only and are not to be construed as limiting the invention.

EXAMPLE 1

(2-Fluorophenyl)[3-[1-methyl-4-piperidinyl)hydroxymethyl]-2-thienyl]methanone

To a stirred solution of 2-(2-fluorobenzoyl)-3-thiophene carboxaldehyde (20.3 g) and tetrahydrofuran (400 ml) cooled to −78° C., under nitrogen, was added via syringe, N-methyl-4-piperidinylmagnesium chloride, prepared from N-methyl-4-chloropiperidine (29.4 g) according to the procedure of J. T. Strupczewski, et al., *J. Med. Chem.* 28, 761(1985), followed by dilution with tetrahydrofuran (40 ml). The solution was stirred for 2 hrs 40 mins at −78° C. Dilute aqueous ammonium chloride solution was added and the mixture was allowed to warm to room temperature. Ether and dichloromethane were added and the layers separated. The organic layer was washed with dilute aqueous sodium bicarbonate solution. The combined aqueous layers were back-extracted with dichloromethane, and the combined organic layers were washed with brine, dried over anhydrous potassium carbonate, filtered, and concentrated. The residue was purified by flash chromatography (silica gel, 5% triethyl amine/0–95% ethyl acetate/hexane) to afford 10.0 g (35%) of product, as a foam. Trituration with ether followed by recrystallization from ether-ethyl acetate-pentane provided the analytical sample, m.p. 133.5°–135.5° C.

| ANALYSIS: | | | |
|---|---|---|---|
| Calculated for $C_{18}H_{20}FNO_2S$: | 64.83% C | 6.06% H | 4.20% N |
| Found: | 64.92% C | 6.09% H | 4.13% N |

EXAMPLE 2

4-(1-Methyl-4-piperidinyl)thieno[3,2-c][1]benzoxepine-10(4H)-one fumarate

To a stirred solution of (2-fluorophenyl)[3-[(1-methyl-4-piperidinyl)-hydroxymethyl]-2-thienyl]methanone (6.00 g) and tetrahydrofuran (225 ml), cooled to −78° C., was added potassium tert-butoxide (2.22 g) in two portions. The solution was allowed to warm slowly to 0° C. over 2 hr. The temperature was maintained at −5°–0° C. for an additional 2.5 hrs, and dilute aqueous sodium bicarbonate solution was added. Ether and dichloromethane were added and the layers separated. The organic layer was washed with dilute aqueous sodium bicarbonate solution, and the combined aqueous layers were back-extracted with dichloromethane. The combined organic layers were washed with brine, dried over anhydrous sodium sulfate, filtered, and concentrated. The residue was purified by flash chromatography (silica gel, 3% triethyl amine/0–5% methanol/dichloromethane) followed by a second flash chromatography (alumina, 3% triethyl amine/0–2.5% methanol/ethyl acetate) to afford 2.46 g (61%) of the basic product, as an oil. The basic product was converted to the fumarate by treatment with fumaric acid in methanol. Recrystallization from methanol-dichloromethane-pentane gave the analytical product, m.p. 177°–170° C.

| ANALYSIS: | | | |
|---|---|---|---|
| Calculated for $C_{18}H_{19}NO_2S \cdot C_4H_4O_4$: | 61.52% C | 5.41% H | 3.26% N |
| Found: | 61.62% C | 5.37% H | 3.29% N |

EXAMPLE 3

7-Fluoro-4-(1-methyl-4-piperidinyl)-thieno[3,2-c][1]benzoxepin-10(4H)-one sesquifumarate To a stirred solution of 2,4-difluorophenyl[3-[(1-methyl-4-piperidinyl)-hydroxymethyl]-2-thienyl]methanone (3.70 g) and tetrahydrofuran (250 ml), cooled to −78° C. under nitrogen, was added potassium tert-butoxide (1.42 g). The solution was allowed to warm slowly to −10° C. The temperature was maintained at −10°−−5° C. for an additional 3 hrs and dilute aqueous sodium bicarbonate solution and ether were added. The layers were separated and the aqueous layer was extracted with ether. The combined organic layers were washed with brine, dried over anhydrous potassium carbonate, filtered, and concentrated. The residue was purified by flash column chromatography (silica gel, 3% triethylamine/1% methanol/dichloromethane) to afford 2.3 g (66%) of the basic product as an oil. The oil was treated with fumaric acid in methanol. The mixture was concentrated and diisopropyl ether was added to provide the analytical sample, m.p. 188°–190° C.

| ANALYSIS: | | | |
|---|---|---|---|
| Calculated for $C_{24}H_{24}FNO_8S$: | 57.02% C | 4.79% H | 2.77% N |
| Found: | 57.08% C | 4.79% H | 2.75% N |

EXAMPLE 4

4-Hydroxy-4-(1-methyl-4-piperidinyl)naphtho[2,3-b]thiophen-9(4H)-one hydrochloride To a stirred solution of (2-fluorophenyl)[3-[(1-methyl-4-piperidinyl)-hydroxymethyl]-2-thienyl]methanone (15.0 g) and dimethylformamide (150 ml), cooled to 0° C. under nitrogen, was added potassium tert-butoxide (5.55 g). The solution was stirred at 0° C. for 1 hr and then poured into ethyl acetate and water. The layers separated and the organic layer was washed with water, and filtered. The filter cake was washed with ethyl acetate and ether to afford 7.80 g (55%) of the basic product.

The hydrochloride was prepared by slurrying the basic product in 2-propanol, adding methanolic-hydrogen chloride, and then isopropyl ether to give the analytical sample, m.p. 251°–253° C.

| ANALYSIS: | | | |
|---|---|---|---|
| Calculated for $C_{18}H_{19}NO_2S \cdot HCl$: | 61.79% C | 5.76% H | 4.00% N |
| Found: | 61.78% C | 5.52% H | 3.92% N |

EXAMPLE 5

α-[2-[(2-Fluorophenyl)methyl]-3-thienyl]-1-methyl-4-piperidinemethanol

To a stirred solution of 2-[(2-fluorophenyl)methyl]-3-thiophenecarboxaldehyde (24.0 g) and tetrahydrofuran (500 ml) cooled to −78° C. under nitrogen, was added, via syringe, N-methyl-4-piperidinylmagnesium chloride, prepared from N-methyl-4-chloropiperdine (49.3 g) according to the procedure of J. T. Strupczewski, et al., *J. Med. Chem.* 28, 761 (1985), over 1 hr, followed by dilution with tetrahydrofuran (75 ml). The solution was stirred 1 hr while being allowed to slowly warm to 0° C., and maintained at 0° C. for an additional 2 hrs 10 mins. Dilute aqueous sodium bicarbonate solution, ether, and dichloromethane were added, and the layers separated. The organic layer was washed with dilute aqueous sodium bicarbonate solution. The combined aqueous layers were back-extracted with dichloromethane, and the combined organic layers were washed with brine, dried over anhydrous potassium carbonate, and filtered. The filtrate was concentrated and the residue was purified by flash chromatography (silica gel, 0–45% methanol/dichloromethane) to afford 24.7 g (71%) of product, as a foam. Trituration with ether-pentane followed by recrystallization from ether-dichloromethane-pentane gave the analytical sample, m.p. 110.5°–112.5° C.

| ANALYSIS: | | | |
|---|---|---|---|
| Calculated for $C_{18}H_{22}FNOS$: | 67.67% C | 6.95% H | 4.39% N |
| Found: | 67.51% C | 7.07% H | 4.37% N |

EXAMPLE 6

α-[2-[(2-Fluorophenyl)(1-(ethoxy)ethoxy)methyl]-3-thienyl]-1-methyl-4-piperidinemethanol To 3-thiophenecarboxaldehyde dimethyl acetal (11.9 g) and ether (180 ml) was added n-butyllithium (31.0 ml, 2.5M in hexanes) at a rate so as to maintain gentle reflux of the solvent. The mixture was heated under reflux for 0.5 hr, cooled to ambient temperature, diluted with tetrahydrofuran (50 ml), was cooled to −78° C., and 2-fluorobenzaldehyde (8.50 ml) in tetrahydrofuran (90 ml) was added. The reaction mixture was allowed to warm to ambient temperature over several hrs and was quenched with dilute aqueous ammonium chloride solution and ether. The layers were separated and the organic layer was washed with dilute aqueous ammonium chloride solution. The combined aqueous layers were back-extracted with ether, and the combined organic layers were washed with brine, dried over anhydrous potassium carbonate, and filtered. Concentration of the residue afforded 3-(dimethoxymethyl)-α-(2-fluorophenyl)-2-thiophenemethanol.

To a stirred slurry of acidic silica gel (prepared from 36 g of silica gel, 120 ml of dichloromethane, and 6.6 ml of 15% aqueous sulfuric acid) was added 3-(dimethoxymethyl)-α-(2-fluorophenyl)-2-thiophenemethanol in dichloromethane (45 ml). The reaction mixture was stirred at room temperature for 1.5 hrs, poured over anhydrous potassium carbonate, and filtered. Concentration of the filtrate gave 2-[(2-fluorophenyl)hydroxymethyl]-3-thiophenecarboxaldehyde.

A solution of 2-[(2-fluorophenyl)hydroxymethyl]-3-thiophenecarboxaldehyde in ethyl vinyl ether (70 ml) and p-toluenesulfonic acid hydrate (5 mg) was stirred at ambient temperature for 1 to 2 hrs. The reaction mixture was stirred over anhydrous potassium carbonate, filtered, and concentrated to 2-[(2-fluorophenyl)(1-(ethoxy)ethoxy)methyl]-3-thiophenecarboxaldehyde.

To a stirred solution of the 2-[(2-fluorophenyl)(1-(ethoxy)ethoxy)methyl]-3-thiophenecarboxaldehyde and tetrahydrofuran (400 ml), cooled to −78° C. under nitrogen, was added, via syringe, N-methyl-4-piperidinylmagnesium chloride over 1.5 hrs. (the Grignard reagent was prepared from N-methyl-4-chloropiperidine (29.4 g) according to the procedure of J. T. Strupczewski, et al., et al., *J. Med. Chem.*, 28, 761 (1985), followed by dilution with tetrahydrofuran (45 ml)). The solution was allowed to warm slowly to −20° C. over 2.5 hrs, and dilute aqueous ammonium chloride solution and ether were added. The layers were separated and the organic layer washed with water. The combined aqueous layers were back-extracted with ether, and the combined organic layers washed with brine, dried over anhydrous potassium carbonate, filtered, and concentrated. The residue was purified by flash column chromatography (silica gel, 0–45% methanol/dichloromethane) to afford 6.4 g (20% overall) of α-[2-[2-fluorophenyl(1-(ethoxy)ethoxy)methyl]-3-thienyl]-1-methyl-4-piperidinemethanol.

EXAMPLE 7

α²-(2-Fluorophenyl)-α³-(1-methyl-4-piperidinyl)-2,3-thiophenedimethanol

A solution of α-[2-[(2-fluorophenyl)(1-(ethoxy)ethoxy)methyl]-3-thienyl]-1-methyl-4-piperidinemethanol (5,89 g), tetrahydrofuran (75 ml), and 0.5N hydrochloric acid (75 ml) was stirred at ambient temperature for 3 hrs. The reaction mixture was quenched with dilute aqueous sodium bicarbonate solution. The aqueous layer was extracted with dichloromethane and ether, and the combined organic layers were washed with brine, dried over anhydrous potassium carbonate, filtered and concentrated. The residue was purified by flash column chromatography (silica gel, 3% triethylamine/0–10% methanol/ethyl acetate). Concentration of the appropriate fractions followed by recrystallization from ether/dichloromethane/pentane afforded 1.50 g (31%) of the product, m.p. 137°–140° C.

| ANALYSIS: | | | |
|---|---|---|---|
| Calculated for $C_{18}H_{22}FNO_2S$: | 64.45% C | 6.61% H | 4.18% N |
| Found: | 63.90% C | 6.63% H | 4.19% N |

EXAMPLE 8

2-(2-Fluorobenzoyl)-3-thiophenecarboxaldehyde

To 3-thiophenecarboxaldehyde dimethylacetal (50.6 g) and ether (500 ml) was added n-butyllithium (132 ml, 2.5M in hexanes) at a rate so as to maintain gentle reflux of the mixture. The reaction mixture was heated at reflux an additional 30 mins, diluted with tetrahydrofuran (600 ml), and cooled to 0° C. A solution of 2-fluorobenzoyl chloride (44.0 ml, 368 mmol) and tetrahydrofuran (500 ml), precooled to −78° C., was added with stirring. The mixture was stirred at −78° C. for 1 hr and then allowed to warm to room temperature overnight. Dilute aqueous ammonium chloride solution and ether were added and the layers were separated. The organic layer was washed with dilute aqueous sodium bicarbonate solution, and the combined aqueous layers were back-extracted with ether. The combined organic layers were washed with brine, dried over anhydrous potassium carbonate, filtered, and concentrated to give 2-(2-fluorobenzoyl)-3-thiophenecarboxaldehyde dimethylacetal.

To 2-(2-fluorobenzoyl)-3-thiophenecarboxaldehyde dimethylacetal was added a solution of absolute ethanol (575 ml) and hydrogen chloride (39 g). The reaction mixture was heated at reflux for 10 mins, with stirring under nitrogen. The solution was cooled to room temperature, diluted with water and ether, and the layers were separated. The aqueous layer was extracted with ether, and the combined organic layers washed with dilute aqueous sodium bicarbonate solution, brine, dried over anhydrous potassium carbonate, filtered and concentrated. The residue was purified by flash column chromatography (silica gel, 0–20% ethyl acetate/hexanes) to afford 20.3 g (27%) of product.

EXAMPLE 9

2-(2-(Fluorobenzyl)-3-thiophenecarboxaldehyde

To 2-(2-fluorobenzoyl)-3-thiophenecarboxaldehyde dimethylacetal (144 g), and ethylene glycol (500 ml) was added potassium hydroxide (115 g) and hydrazine-monohydrate (74.8 ml). The reaction mixture was warmed slowly in an oil bath to 70°–75° C.; 10–15 ml of distillate was collected. The temperature was slowly increased to 120°–125° C. and maintained at this temperature for 30 mins. The oil bath was removed, and the mixture allowed to cool to room temperature. Ether and water were added and the layers separated. The aqueous layer was extracted with ether-dichloromethane, and the combined organic layers washed with brine and dried over anhydrous potassium carbonate, filtered and concentrated. The residue in ethyl acetate was passed through a pad of silica gel and ethyl acetate. Concentration afforded 2-(2-fluorobenzyl)-3-thiophenecarboxaldehyde dimethylacetal.

To silica gel (100 g), 15% aqueous sulfuric acid (15.4 g), and dichloromethane (400 ml) was added 2-(2-fluorobenzyl)-3-thiophenecarboxaldehyde dimethylacetal and dichloromethane (25 ml). The mixture was stirred for 2.5 hrs. The reaction mixture was filtered. The filter cake was washed with ethyl acetate and dichloromethane. The filtrate was concentrated and the residue was purified by flash column chromatography (silica gel, 0.5–10% ethyl acetate/hexanes) to afford 24.0 g (23.5%) of 2-(2-fluorobenzyl)-3-thiophenecarboxaldehyde.

We claim:

1. A compound of the formula

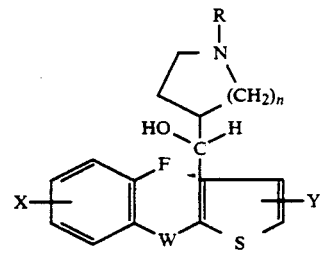

wherein R is loweralkyl or arylloweralkyl; X and Y are independently hydrogen, loweralkyl, halogen, loweralkoxy, or trifluoromethyl; W is $CH_2$, CHOH, or C=O; and n is 1 or 2; an optical isomer or pharmaceutically acceptable addition salt thereof.

2. A compound according to claim 1 wherein n is 2.

3. The compound according to claim 2 which is (2-fluorophenyl)[3-[(1-methyl-4-piperidinyl)hydroxymethyl]-2-thienyl]methanone.

4. The compound according to claim 2 which is α-[2-[(2-fluorophenyl)methyl]-3-thienyl]-1-methyl-4-piperidinemethanol.

5. The compound according to claim 2 which is α²-(2-fluorophenyl)-α³-(1-methyl-4-piperidinyl)-2,3-thiophenedimethanol.

6. A method of alleviating pain in a mammal by administering to a mammal in need of pain alleviation a pain alleviating effect amount of a compound of claim 1.

7. A composition comprising a pain alleviating effective amount of a compound of claim 1 and a pharmaceutically acceptable adjuvant therefor.

* * * * *